(12) United States Patent
Matthias et al.

(10) Patent No.: US 9,919,982 B2
(45) Date of Patent: Mar. 20, 2018

(54) METHOD AND DEVICE FOR GAS PROCESSING

(71) Applicant: Airbus DS GmbH, Taufkirchen (DE)

(72) Inventors: Carsten Matthias, Friedrichshafen (DE); Walter Jehle, Horgenzell (DE)

(73) Assignee: Airbus DS GmbH, Taufkirchen (DE)

( * ) Notice: Subject to any disclaimer, the term of this patent is extended or adjusted under 35 U.S.C. 154(b) by 0 days.

(21) Appl. No.: 14/755,430

(22) Filed: Jun. 30, 2015

(65) Prior Publication Data
US 2016/0009608 A1 Jan. 14, 2016

(30) Foreign Application Priority Data
Jul. 8, 2014 (EP) .................................... 14176209

(51) Int. Cl.
*C07C 1/12* (2006.01)
*C10L 3/10* (2006.01)
(Continued)

(52) U.S. Cl.
CPC ............... *C07C 1/12* (2013.01); *B01D 53/04* (2013.01); *B01D 53/047* (2013.01); *B01D 53/0462* (2013.01); *B01D 53/1425* (2013.01); *B01D 53/1443* (2013.01); *B01D 53/1493* (2013.01); *B01D 53/229* (2013.01); *B01D 63/00* (2013.01); *C07C 7/11* (2013.01); *C07C 7/12* (2013.01); *C10L 3/08* (2013.01); *C10L 3/104* (2013.01); *C12M 47/18* (2013.01); *B01D 53/0438* (2013.01); *B01D 2053/221* (2013.01); *B01D 2252/204* (2013.01); *B01D 2253/20* (2013.01); *B01D 2256/245* (2013.01); *B01D 2257/504* (2013.01); *B01D 2258/05* (2013.01); *B01D 2259/40088* (2013.01); *B01D 2259/65* (2013.01); *B01D 2313/40* (2013.01);
(Continued)

(58) Field of Classification Search
CPC .... C07C 7/12; C07C 1/12; C07C 9/04; Y02C 10/08; Y02C 10/10; B01D 2258/05; B01D 2257/504; B01D 2313/40; B01D 2252/204; B01D 53/0438
USPC ............................................... 518/722; 95/45
See application file for complete search history.

(56) References Cited

U.S. PATENT DOCUMENTS

2009/0156875 A1* 6/2009 Tomioka ................ B01D 3/101
585/802
2009/0162914 A1* 6/2009 Offerman ................ C12P 5/023
435/167
(Continued)

FOREIGN PATENT DOCUMENTS

DE    10 2009 018 126 A1   10/2010
DE       102011103430 A1   12/2012
(Continued)

OTHER PUBLICATIONS

European Search Report dated Apr. 10, 2015 in corresponding EP application No. 14176209.6 (partial English translation).
(Continued)

Primary Examiner — Jafar Parsa
(74) Attorney, Agent, or Firm — Posz Law Group, PLC

(57) ABSTRACT

A method for gas processing, in particular for processing biogas of a biogas plant in which in one method step a membrane process or a reactive process is executed, and in at least one further method step an adsorption and/or absorption process is executed.

13 Claims, 7 Drawing Sheets

Figure 1:
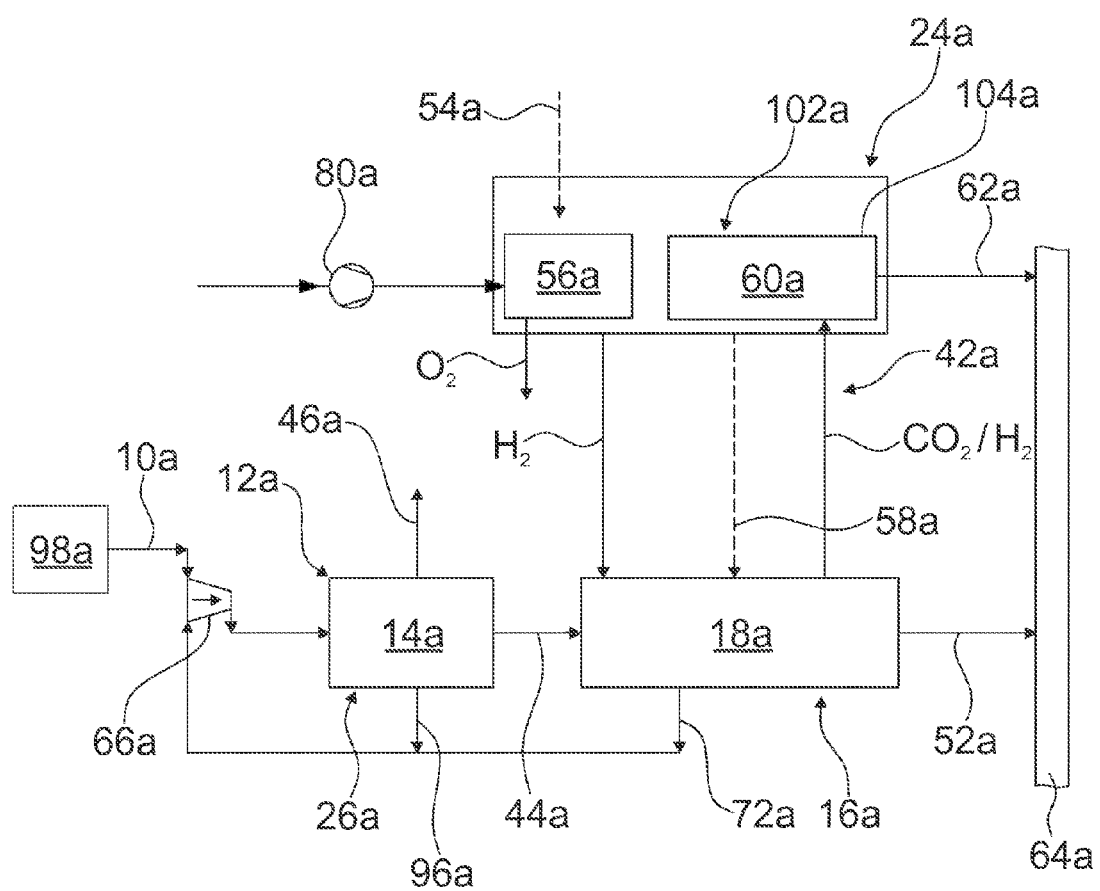

(51) Int. Cl.
*C10L 3/08* (2006.01)
*C07C 7/12* (2006.01)
*B01D 63/00* (2006.01)
*B01D 53/14* (2006.01)
*B01D 53/04* (2006.01)
*C12M 1/00* (2006.01)
*B01D 53/047* (2006.01)
*B01D 53/22* (2006.01)
*C07C 7/11* (2006.01)

(52) U.S. Cl.
CPC ............... *Y02C 10/08* (2013.01); *Y02C 10/10* (2013.01); *Y02E 50/343* (2013.01); *Y02P 20/152* (2015.11); *Y02P 20/59* (2015.11)

(56) References Cited

U.S. PATENT DOCUMENTS

| | | | | |
|---|---|---|---|---|
| 2011/0012063 | A1* | 1/2011 | Assa | B01D 53/1425 252/372 |
| 2011/0094378 | A1 | 4/2011 | Mitariten | |
| 2011/0185896 | A1* | 8/2011 | Sethna | B01D 53/002 95/45 |
| 2012/0091730 | A1* | 4/2012 | Stuermer | C25B 1/04 290/1 R |
| 2012/0107895 | A1* | 5/2012 | Nirmalakhandan | C12M 21/04 435/168 |
| 2012/0160098 | A1* | 6/2012 | Papale | B01D 53/0438 95/106 |
| 2012/0228553 | A1 | 9/2012 | Tirio | |
| 2014/0053724 | A1 | 2/2014 | Raatscher et al. | |

FOREIGN PATENT DOCUMENTS

| | | |
|---|---|---|
| EP | 2 438 975 A1 | 4/2012 |
| EP | 2468384 A1 | 6/2012 |
| EP | 2532729 A2 | 12/2012 |
| EP | 2682450 A2 | 1/2014 |
| WO | 2011097162 A1 | 8/2011 |

OTHER PUBLICATIONS

Office Action dated Jun. 30, 2017 issued in corresponding EP patent application No. 14176209.6 (and partial English translation).

* cited by examiner

METHOD AND DEVICE FOR GAS PROCESSING

CROSS REFERENCE TO RELATED APPLICATION

This application is based on and incorporates herein by reference European Patent Application No. 14176209.6 filed on Jul. 8, 2014.

STATE OF THE ART

From EP 2 438 975 A1 a method and a device are known, which comprise an adsorber made of an adsorber resin. In an adsorption phase raw biogas is conveyed through the adsorber under ambient pressure. In a regeneration phase the adsorber is regenerated at temperatures between 20° C. and 100° C. by a purging gas.

An objective of the invention is, in particular, to provide a method having a high efficiency rate and/or a method allowing a compact device. The objective is achieved according to the invention by the features of patent claim 1, while advantageous implementations and further developments of the invention may be gathered from the subclaims and one coordinate claim.

Advantages of the Invention

A method for gas processing, in particular for processing biogas of a biogas plant, is proposed, in which in one method step a membrane process or a reactive process is executed and in at least one further method step an adsorption and/or absorption process, in particular for a precision gas purification to achieve a high level of methane purity, is executed. By the adsorption and/or absorption process being executed in a "further method step" is to be understood, in this context, in particular that an adsorption and/or absorption material is arranged such that it is separate, in particular spaced apart, in particular at a distance greater than 1 cm, from a membrane and/or that the method steps can also be carried out separately and independently from each other. A "reactive process" is to be understood, in this context, in particular as a process in which a gas mixture, in particular an at least methane-rich gas mixture, is generated, in particular in a catalytically activated chemical process or biological process, in particular with a nutrient substrate. Especially preferably, in the reactive process at least a methane-rich gas mixture is generated from a $CO_2$ source in a power-to-gas plant. Herein preferentially biogas is utilized as a $CO_2$ source. A "power-to-gas plant" is herein to be understood, in particular, as a plant in which electrical energy from a plant, in particular a wind power plant and/or a solar plant, is used to generate hydrogen via electrolysis. This hydrogen is then used, in particular, together with carbon dioxide in particular from a biogas plant or from another $CO_2$ source, to generate methane by means of a catalyst. The methane can be fed into a natural gas grid, in particular after a precision $CO_2$ gas purification by means of an adsorption and/or absorption unit and after a methane dehydration. Besides the precision $CO_2$ gas purification, the adsorption and/or absorption unit preferably also fulfills the function of residual methane dehydration to very low dew point temperatures in the product gas methane.

In the combination of the method steps of a membrane process and an adsorption and/or absorption process, saving of a membrane stage of an in particular multi-stage membrane plant and thus a considerable downsizing of a membrane plant, preferably by more than a third, is achievable. Furthermore, a particularly simple membrane module interconnection is achievable, and particularly high gas qualities, in particular bio-natural gas qualities with a methane purity greater than 99.5 volume percent, are achievable, in particular if the adsorption and/or absorption process is executed as a subsequent purification, in which the adsorption and/or absorption process is in particular executed as a precision purification in which preferably a diminishing of a $CO_2$ concentration in the process gas to less than 0.3 volume percent of $CO_2$ is executed. The adsorption and/or absorption process can herein be used to process the retentate and/or the permeate of a membrane module, i.e. at respective high or low pressures. Moreover, lowering a feed pressure of the membrane plant is possible and thus a reduction of operative costs of a plant. Further a downsizing of a heat exchanger of the membrane plant, which is required for feed gas cooling, is possible. A "bio-natural gas" is to be understood, in this context, in particular as methane that is not of fossil origin but has been generated from biogenic materials.

In the combination of the method steps of a reactive process and an adsorption and/or absorption process, a particularly high gas quality, in particular bio-natural gas quality with a methane purity greater than 99.5 volume percent, is achievable, in particular if the reactive process is executed as a catalytic methanization process and the $CO_2$ contained in the bio-natural gas is catalytically converted with, $H_2$ from a power-to-gas plant, into methane and water, and directly following this an adsorption and/or absorption process is executed as a subsequent purification, wherein the adsorption and/or absorption process is in particular executed as a precision purification in which a diminishing of a $CO_2$ concentration in the process gas preferably to less than 0.3 volume percent is executed. However, a method step with a membrane process, a method step with a reactive process and a method step with an adsorption and/or absorption process can also be combined in a variety of versions that are deemed expedient by a person having ordinary skill in the art.

Principally different adsorber and/or absorber materials are conceivable, which are deemed expedient by the person having ordinary skill in the art, in particular liquid or gaseous adsorber and/or absorber materials. Particularly preferably, however, at least one solid-matter adsorber and/or solid-matter absorber is utilized, namely particularly preferably an adsorber and/or absorber resin. An amine, preferentially a solid amine, is particularly suitable. The adsorber and/or absorber material herein preferably has, at standard conditions, i.e. at a temperature of 25° C. and a pressure of 1 $bar_{abs}$, a selectivity greater than 100, especially preferably greater than 150 and very preferably greater than 200. A "selectivity" is herein to be understood as a load ratio, in particular a solid-amine load ratio, in particular a load ratio of $CO_2$ and $CH_4$. The adsorber and/or absorber material is preferably applied as a filling. By a "filling" is to be understood, in this context, in particular that the material is present in a granular and/or fragmented mixture that is present such that it is pourable. With a solid amine, advantageously low regeneration temperatures are achievable, on account of which particularly preferably waste heat from other units, e.g. in particular a block heating and power station (BHKW), from a membrane unit and/or from a power-to-gas plant, may be used. Furthermore, a long service life and a particularly high gas purity are achievable. However, principally molecular sieves, e.g. made of activated charcoal, are also conceivable alternatively to an amine.

In a further implementation of the invention it is proposed that at least one adsorption and/or absorption unit is cooled or heated in at least one method step, whereby the adsorption and/or absorption process and/or a regeneration process can be supported especially advantageously. "Cooled" or "heated" is to mean, in particular, that heat is conveyed off and/or fed in actively, in particular by means of a third unit. Preferably a so-called temperature swing adsorption and/or absorption is executed, in which an adsorption and/or absorption is executed at a low temperature and a regeneration is executed at a higher temperature. Herein the adsorption and/or absorption takes place advantageously at a temperature of less than 40° C., preferably less than 30° C. and very particularly preferably less than 20° C., whereas the regeneration is executed advantageously at a temperature greater than 70° C., preferably at a temperature greater than 80° C. and very particularly preferably greater than 90° C. Preferably, however, the regeneration is executed at a temperature of less than 120° C.

Preferentially, at the start of the regeneration of the adsorption and/or absorption unit a methane recovery is carried out by means of a vacuum pump.

If heat energy is transferred from at least one adsorption and/or absorption unit to at least one further adsorption and/or absorption unit, and/or if pressure energy is transferred from at least one adsorption and/or absorption unit to at least one further adsorption and/or absorption unit, it is possible, by an advantageous heat integration respectively pressure integration, to save energy and to achieve a high efficiency rate. Preferably herein a plurality of adsorption and/or absorption units are interconnected with each other. Preferably the adsorption and/or absorption units are alternately mutually pressurized or evacuated. Advantageously a so-called pressure swing adsorption and/or absorption is executed, in which at a higher pressure an adsorption and/or absorption is executed and at a lower pressure a regeneration is executed.

It is also proposed that for a temperaturizing, i.e. cooling and/or heating, of an adsorption and/or absorption unit waste heat is utilized, in particular waste heat of a power plant, in particular of a block heating and power station, and/or waste heat of the membrane process, and/or very particularly preferably from a power-to-gas plant, as a result of which energy can be saved. In a power-to-gas plant the waste heat preferably of an electrolyzer and/or released reaction heat of the catalytic methanization may be used for a regeneration of an adsorber and absorber material. In particular for a cooling in the adsorption and/or absorption process a cooling installation can be used which utilizes waste heat for generating coldness. Especially advantageously a plurality of adsorption and/or absorption units are interconnected with each other, and a heat integration of the adsorption and/or absorption units is implemented with each other by means of a turned-over heat exchanger fluid, and/or in combination with a block heating and power station and/or with a membrane unit and/or with the power-to-gas plant. An adsorption and/or absorption heat resulting during the $CO_2$ adsorption and/or absorption may advantageously be fed to the biogas plant. In the methane production (methanization) in a power-to-gas plant heat is released by the exothermic reaction $CO_2+4H_2 \leftarrow\rightarrow CH_4+2H_2O$, which heat can be utilized preferably in the biogas plant and/or advantageously in a respective method according to the invention, in particular for the regeneration of the adsorption and/or absorption unit.

In a further implementation of the invention it is proposed that hydrogen, in particular from a power-to-gas plant, is fed to at least one adsorption and/or absorption unit. Herein the hydrogen is preferably introduced into the adsorption and/or absorption unit during a regeneration, on account of which the regeneration can be executed particularly efficiently, in particular due to an achievable increased heat conductivity of an adsorption and/or absorption material in an $H_2$ atmosphere, preferably due to an increased heat conductivity of a filling of an adsorption and/or absorption resin. The regeneration takes place preferably at increased pressure—i.e. in particular at a pressure greater than 2 $bar_{abs.}$ and particularly advantageously greater than 4 $bar_{abs.}$—and in an $H_2$ atmosphere. At the end of a desorption, the reagents $H_2$ and $CO_2$ are preferably discharged to the power-to-gas plant at such a high pressure level that in a following methanization the product gas methane can be fed into the natural gas grid directly, without subsequent densification. Thus inside the power-to-gas plant a pressure increase before an electrolysis is achievable in an energetically particularly favorable manner. A regeneration without feeding hydrogen into the adsorption and/or absorption unit preferably takes place at a pressure of less than 1.5 $bar_{abs.}$ The adsorption and/or absorption unit and in particular a filling of adsorption and/or absorption resin contained therein may advantageously fulfill a function of a $CO_2$ storage and of a gas premixing for a directly following methanization in the power-to-gas plant. Moreover, the reagents $H_2$ and $CO_2$ for the methanization may be obtained at increased pressure, which has a favorable impact on a balance situation and on an achievable turnout of the methanization. The regeneration of the adsorption and/or absorption unit, in particular the regeneration of a filling of adsorption and/or absorption resin in a hydrogen atmosphere, is advantageously regulated, via the hydrogen feed-in as well as via a regeneration pressure and a temperature, in such a way that the reagents $H_2$ and $CO_2$ for a directly following methanization in the power-to-gas plant can be conveyed out of the adsorption and/or absorption unit at least substantially in the stoichiometric ratio. Herein by "at least substantially" is to be understood, in particular, that there is a deviation of less than 20% and particularly preferentially of less than 10%.

Furthermore, a device for executing a method according to the invention is proposed. Herein the device comprises in particular a membrane unit and/or at least a plant connection for connecting a reactive plant and an adsorption and/or absorption unit, which allow the membrane process and/or the reactive process and the adsorption and/or absorption process to be executed in separate method steps. The plant connection is herein provided, in particular, to interconnect the reactive plant, e.g. in particular a power-to-gas plant, with the membrane unit and/or in particular with the first adsorption and/or absorption unit.

Hydrogen produced in the power-to-gas plant can be fed to the adsorption and/or absorption unit, wherein, in particular preferably during the regeneration, the hydrogen is introduced into the adsorption and/or absorption unit. In an $H_2$ atmosphere a high-grade heat conductivity of the adsorption and/or absorption material, in particular of an adsorption and/or absorption resin, preferably implemented as a filling, is achievable. Moreover as already mentioned above the adsorption and/or absorption unit, in particular a filling of adsorption and/or absorption resin contained therein, may advantageously fulfill the functions of a $CO_2$ storage and of a gas premixing for a directly following methanization in the power-to-gas plant. Furthermore the reagents $CO_2$ and $H_2$ are obtainable for the methanization at increased pressure, which has a favorable impact on a balance situation and on an achievable turnout of the methanization.

"Provided" is to mean in this context, in particular, specifically designed and/or equipped. By an object being provided for a certain function is to be understood, in particular, that the object fulfills said certain function in at least one application state and/or operation state.

It is further proposed that in the device a released reaction heat of a methanization or a waste heat of an electrolyser of the power-to-gas plant can be used in the adsorption and/or absorption unit, in particular in a regeneration of the adsorption and/or absorption unit, respectively that the device is provided for such a utilization.

Preferentially the device comprises at least one heating and/or cooling unit, as a result of which advantageously an active heating and/or active cooling can be executed as has been described above.

If the heating and/or cooling unit comprises at least one heat exchanger, a particularly effective heat transfer is achievable, in particular if at least one adsorption and/or absorption element is integrated in the heat exchanger. Herein the term "integrated" is to mean, in particular, that parts of the heat exchanger are filled and/or coated with an adsorption and/or absorption material. Particularly preferably the heat exchanger comprises at least one tube, which is at least partially filled with an adsorption and/or absorption material, especially advantageously with a resin and very particularly preferably with a resin filling, in particular a solid-matter amine-resin filling. The biogas is herein preferentially conveyed in the tube, through the adsorption and/or absorption material, in particular through the resin filling. A heat carrier fluid is then preferably conveyed in a shell space of the heat exchanger, which may preferably be embodied as a tube bundle heat exchanger.

In a further implementation it is proposed that the at least one tube comprises at least one first and one second wall, and that the adsorption and/or absorption material is at least partially arranged between the walls, as a result of which the adsorption and/or absorption material is advantageously heatable from within and from without. As an alternative, the tube can, however, also comprise only one wall.

DRAWINGS

Further advantages may be gathered from the following description of the drawings. In the drawings three exemplary embodiments of the invention are depicted. The drawings, the description and the claims contain a plurality of features in combination. The person having ordinary skill in the art will expediently also consider the features separately and will further combine them in a purposeful way.

Figure 2:
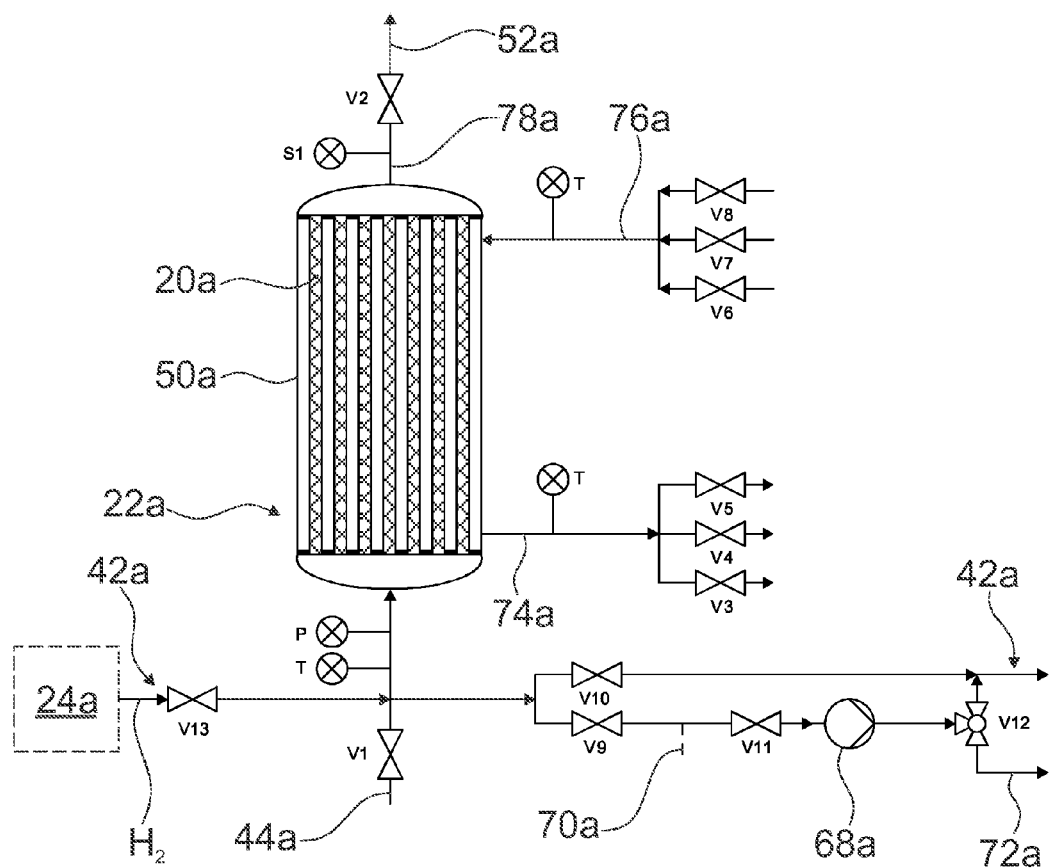
Figure 3:
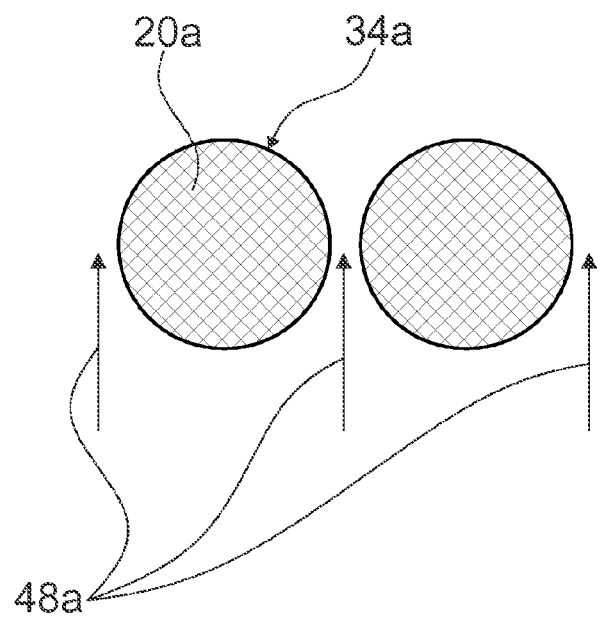
Figure 4:
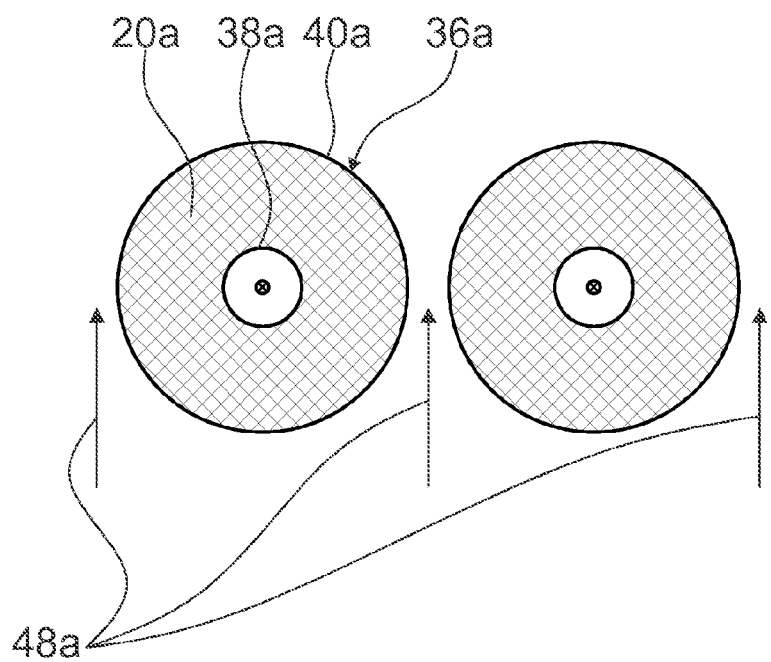
Figure 5:
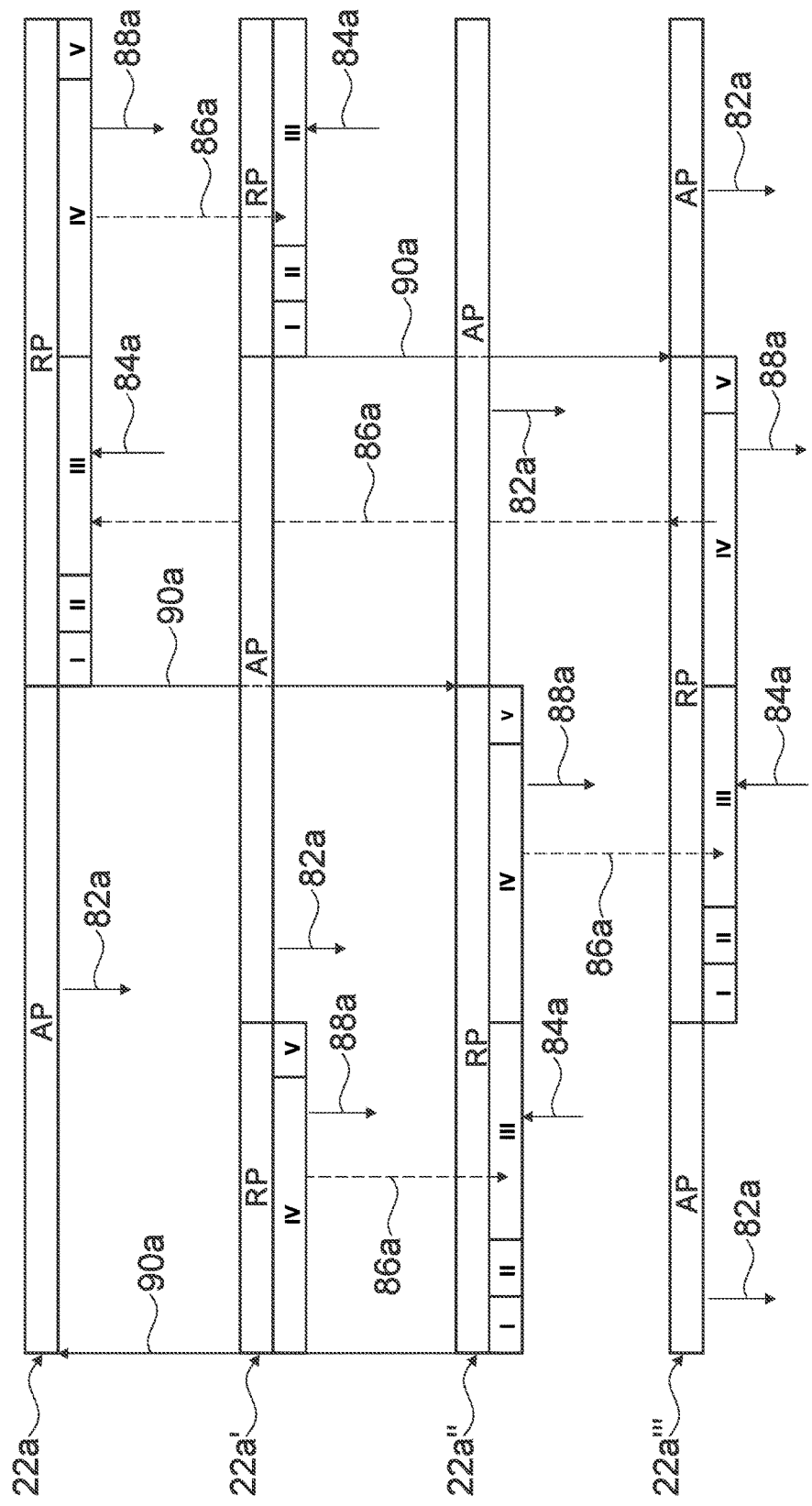
Figure 6:
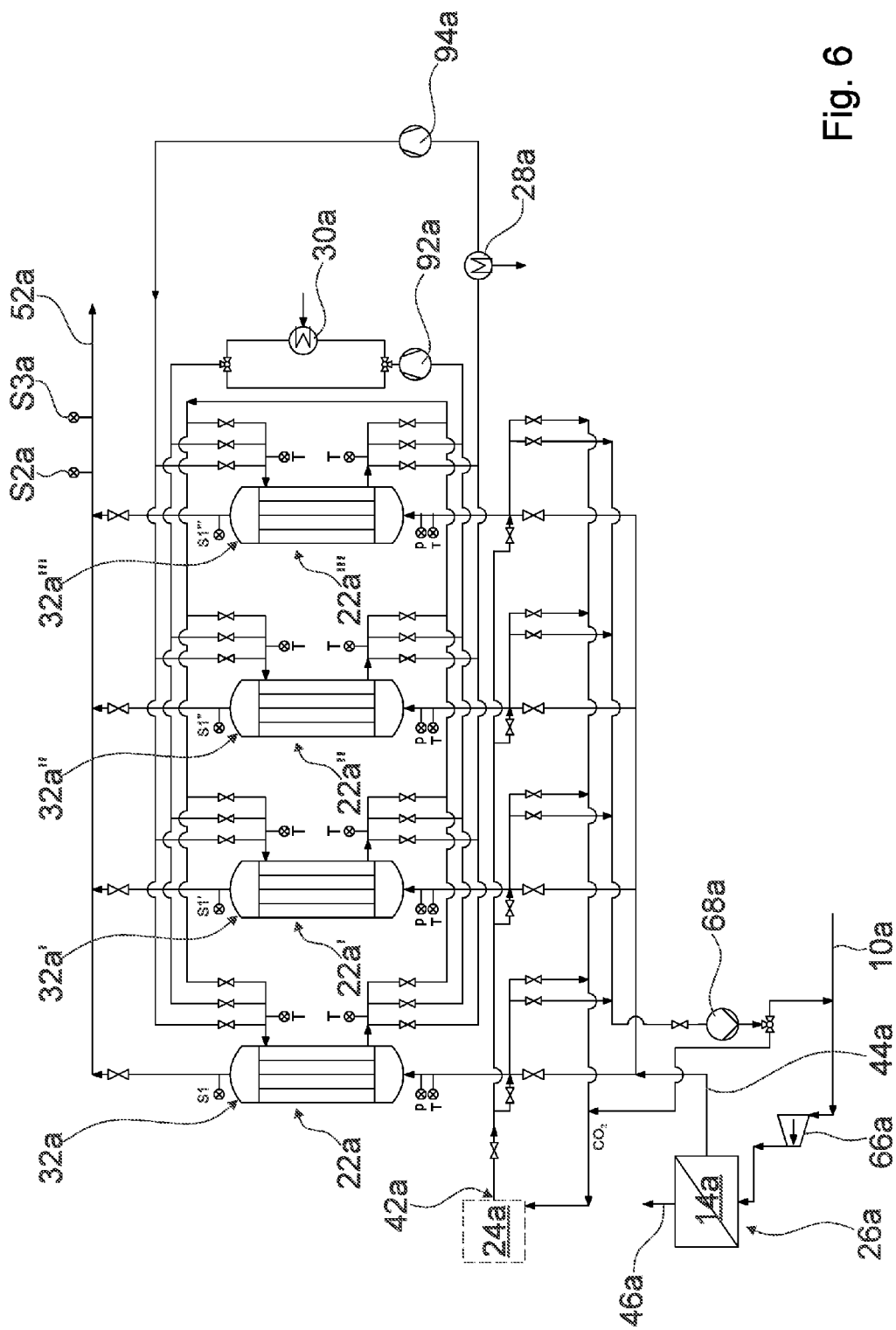
Figure 7:
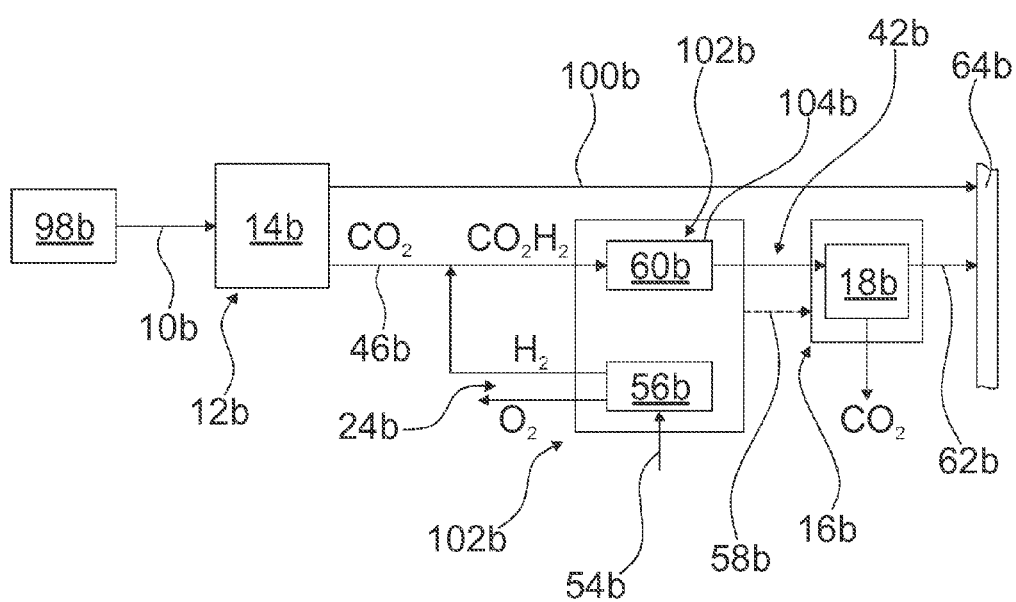
Figure 8:
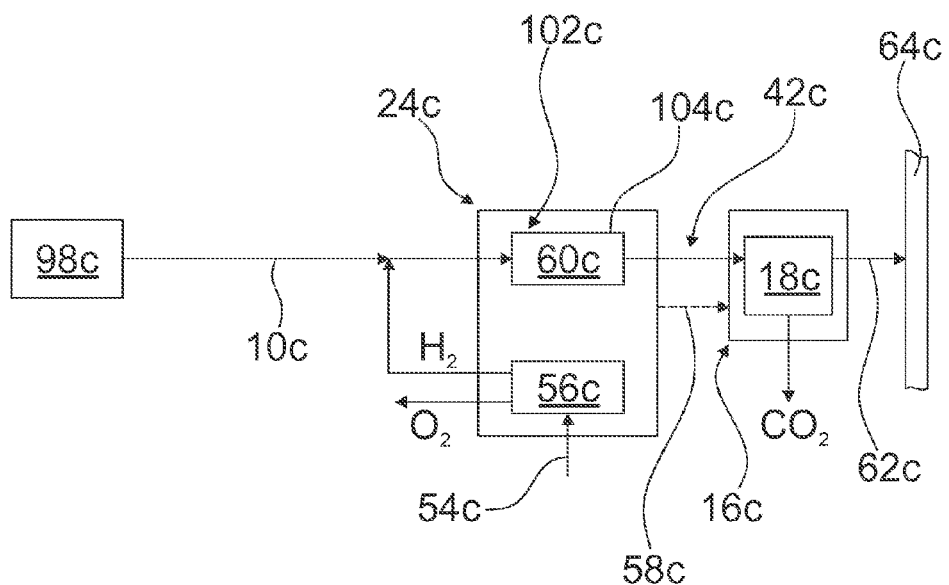

It is shown in:

FIG. 1 a simplified process graphic with a membrane unit,

FIG. 2 a schematically depicted portion of a device according to the invention with an absorption unit, FIG. 3 a schematically depicted portion of a sectional view through the absorption unit of FIG. 2, FIG. 4 a schematically depicted portion of a sectional view through an absorption unit that is an alternative to the absorption unit shown in FIG. 2, FIG. 5 in a simplified presentation process flows of a plurality of interconnected absorption units, and FIG. 6 a simplified presentation of a flow chart of the device, FIG. 7 another simplified process presentation with a membrane unit and a power-to-gas plant, and FIG. 8 a further simplified process presentation with a power-to-gas plant and without a membrane unit.

DESCRIPTION OF THE EXEMPLARY EMBODIMENTS

FIG. 1 shows a simplified process presentation respectively a simplified presentation of a method according to the invention for gas processing, namely for processing biogas 10a in a biogas plant 98a, in which in one method step 12a for separating off $CO_2$ from the biogas 10a, a membrane process 14a is executed in a membrane unit 26a, and in a further, downstream-connected method step 16a an absorption process 18a is executed in absorption units 22a, 22a', 22a", 22a''' (cf. FIGS. 1, 2 and 6). In the membrane unit 26a hollow-fiber membranes are applied (not shown in detail), other membranes deemed expedient by the person having ordinary skill in the art being principally also conceivable. The biogas 10a is conveyed to the membrane unit 26a by means of a compressor 66a, in this case the biogas 10a is pumped through the hollow-fiber membranes. The membrane process 14a, which is implemented as a multi-stage membrane process 14a by means of a re-feed 96a, is executed as a preliminary purification, in particular for a reduction of a $CO_2$ concentration in the biogas 10a from approximately 45 volume percent down to 3-5 volume percent of $CO_2$, previous to the absorption process 18a. The absorption process 18a then executes a subsequent purification, namely in particular a precision purification, preferably with increasing concentration of a bio-natural gas 52a to a methane concentration greater than 99%. For the precision purification, a retentate 44a of the membrane unit 26a is conveyed to the absorption units 22a, 22a', 22a", 22a''' by means of the compressor 66a. Principally, however, the absorption units 22a, 22a', 22a", 22a''' could also be used, additionally or as an alternative, for a processing of a permeate 46a of the membrane unit 26a. The permeate 46a herein consists almost completely of $CO_2$ and a portion of $CH_4$ respectively methane of less than 0.5 volume percent. A complete process according to the invention advantageously makes use of the different selectivities of the membrane unit 26a and the absorption units 22a, 22a', 22a", 22a''' for a $CO_2/CH_4$ gas separation.

The method can principally also be carried out merely with a biogas plant 98a or can advantageously be executed in a combination of a biogas plant 98a with further plants that are deemed expedient by the person having ordinary skill in the art, in particular especially advantageously in combination with a power-to-gas plant 24a. To this purpose the device according to the invention comprises a plant connection 42a for connecting a reactive plant, namely for connecting the power-to-gas plant 24a. The power-to-gas plant 24a, which is supplied with water via a water pump 80a, uses power 54a, preferably from plants that obtain power from renewable energy sources, in particular wind power plants, solar plants etc., to generate with the power 54a by means of an electrolysis 56a, $H_2$ and $O_2$ at increased pressure, preferably at a pressure greater than 5 $bar_{abs.}$, in particular at a pressure of at least substantially 10 $bar_{abs.}$ By "at least substantially" is herein to be understood, in particular, that there is a deviation of less than 20% and particularly preferably less than 10%.

The power-to-gas plant 24a is preferably supplied with a constant power quantity to achieve a long service life. To this purpose the power-to-gas plant 24a can be coupled with one or several plants. Principally it is also conceivable that in the power-to-gas plant 24a surplus energy of a plant is used. In the power-to-gas plant 24a methane 62a is generated in a method step 102a in a reactive process 104a.

During regeneration phases of the absorption units 22a, 22a', 22a", 22a''' the hydrogen is introduced into the absorption units 22a, 22a', 22a", 22a''' at increased pressure, and an absorption material located in the absorption units 22a, 22a', 22a", 22a''' is thermically regenerated in an $H_2$ atmosphere. A waste heat 58a of the power-to-gas plant 24a, namely from the electrolysis 56a carried out by an electrolyzer and from a methanization 60a, is used for the regeneration of the absorption material. A released $CO_2/H_2$ gas mixture is then fed to a directly following methanization 60a in the power-to-gas plant 24a under pressure, preferably at least substantially at 10 $bar_{abs.}$, approximately or at least substantially in a stoichiometric ratio of 1:4. The methanization 60a is preferably effected at one pressure level, such that no subsequent densification of the methane 62a resulting from the methanization 60a is required for the feed-in into a natural gas grid 64a. Before the feed-in into the natural gas grid 64a the methane 62a is dehydrated.

FIG. 2 shows a schematically presented section of a device according to the invention for executing the method. The device comprises the membrane unit 26a and the absorption units 22a, 22a', 22a", 22a''' as well as heating and cooling units 28a, 30a, 32a (FIGS. 2 and 6).

In the absorption process 18a a solid-matter absorber 20a is used, namely a solid amine. The solid amine is integrated in apparatuses that are heatable and coolable, namely in heat exchangers of the heating and cooling units 32a, 32a', 32a", 32a''', thus absorption elements are integrated in the heat exchangers (FIGS. 2, 3, 4 and 6). The absorption units 22a, 22a', 22a", 22a''' herein have a structural design that is comparable to that of a tube bundle heat exchanger. The solid amine is filled into tubes 34a as a filling (FIGS. 2, 3 and 4). A heat carrier fluid 48a is conveyed through the heat exchangers on the shell-side. The tubes 34a are embodied such that they are pressure resistant and are made of metal, preferably of high-grade steel. An exterior housing 50a of the heat exchangers respectively of the absorption units 22a, 22a', 22a", 22a''' is not required to be pressure resistant and is made of a plastic material. Principally, however, other materials that are deemed expedient by the person having ordinary skill in the art are conceivable for the tubes 34a as well as for the housing 50a. As an alternative for the tubes 34a, which are implemented having one wall, the absorption units 22a, 22a', 22a", 22a''' could also comprise tubes 36a having a first and a second wall 38a, 40a, the solid amine being in this case arranged in an annular gap between the walls 38a, 40a (FIG. 4). In an operative state the heat carrier fluid 48a flows around the tubes 34a on the shell side, while the heat carrier fluid 48a flows in operation around the tubes 36a on the shell side and inside. A design with the tubes 36a allows a particularly efficient and quick regeneration of the absorption 22a, 22a', 22a", 22a''' respectively of an absorption resin. A design with the tubes 34a is particularly easily manufacturable.

A process gas respectively the retentate 44a from the membrane unit 26a is conveyed in the tubes 34a through the solid amine, which is implemented as a filling. Herein the $CO_2$ is bonded in a highly selective manner to the solid amine during the absorption process 18a, and bio-natural gas 52a can be obtained at exits 78a of the absorption units 22a, 22a', 22a", 22a''' and can be fed into the natural gas grid 64a.

The absorption units 22a, 22a', 22a", 22a''' each comprise a plurality of valves V1, V2, V9-V13 on a gas side and a plurality of valves V3-V8 on a heat carrier fluid side (FIG. 2). At the valves V1, V2, V9-V13 and V3-V8 tube connections are respectively provided.

The valves V1, V2, V9, V10, V11, V13 on the gas side are necessary for the implementation of a PSA (Pressure Swing Absorption) process. The absorption of the $CO_2$ at the solid amine is herein effected at a high pressure, preferably at a pressure between 4 $bar_{abs.}$ and 20 $bar_{abs.}$. The regeneration is effected, in a complete process without a power-to-gas plant 24a, at a low pressure, preferably at a pressure between 0.1 $bar_{abs.}$ and 1.5 $bar_{abs.}$. In a complete process with the power-to-gas plant 24a, the regeneration is effected at an increased pressure, preferably at a pressure between 4 $bar_{abs.}$ and 20 $bar_{abs.}$. Herein $H_2$ is introduced into the tubes 34a of the absorption units 22a, 22a', 22a", 22a''' during the regeneration by means of a valve V13, and the regeneration of the solid amine is executed in a hydrogen atmosphere at increased pressure. The hydrogen supply as well as the regeneration temperature in the tubes 34a is herein regulated in such a way that a molar mixture ratio results in the gas phase of $R_{H2/CO2}=4+/-20\%$.

The valves V9-V12 are necessary to realize a methane recovery via a connection 72a with a vacuum pump 68a at the end of an absorption phase and before a start of the regeneration of the solid amine, and to remove methane 62a by suction from a free gas phase of the resin filling and to re-convey the methane 62a to the compressor 66a, or to feed the methane 62a to the power-to-gas plant 24a via the power-to-gas plant connection 42a (FIGS. 1 and 2). The valves V9-V12 are also necessary for removing $CO_2$ by suction out of the absorption units 22a, 22a', 22a", 22a''' during regeneration phases, namely in the case of an operation without a power-to-gas plant 24a. Furthermore the valves V9-V12 are use to interconnect absorption units 22a, 22a', 22a", 22a''' with each other in the PSA process and to alternately fill or empty the absorption units 22a, 22a', 22a", 22a''', thus minimizing operation times of the vacuum pump 68a and corresponding operation costs. Between the valves V9 and V11, a connection 70a is provided for a further absorption unit 22a', 22a", 22a'''.

The valves V3-V8 on the heat carrier fluid side are necessary to realize a TSA (Temperature Swing Absorption) process. The valves V3-V5 are herein interconnected with a heat carrier fluid outlet 74a, and the valves V6-V8 are interconnected with a heat carrier fluid inlet 76a. The absorption of the $CO_2$ at the solid amine is herein effected at a low temperature, and the regeneration is effected at a high temperature (maximally 110° C.). Herein an absorption heat 82a resulting during the $CO_2$ absorption at the solid amine is conveyed to the biogas plant 98a via the heat carrier fluid outlet 74a, as a result of which the absorption units 22a, 22a', 22a", 22a''' respectively the solid amine fillings are cooled. Furthermore, the absorption units 22a, 22a', 22a", 22a''' are interconnected with each other via the valves V4-V7, to the purpose of realizing a heat integration of the absorption units 22a, 22a', 22a", 22a''' with each other as well as, if applicable, with a block heating and power station, with the membrane unit 26a and/or with the power-to-gas plant 24a. The valves V3-V8 may also be used for heating up and for cooling the absorption units 22a, 22a', 22a", 22a''' during the regeneration of the solid amine.

The absorption units 22a, 22a', 22a", 22a''' each comprise at their respective exit 78a a $CO_2$ sensor S1, S1', S1", S1''', by which a $CO_2$ concentration in the bio-natural gas 52a is measured and by which the process flows absorption and regeneration of absorption units 22a, 22a', 22a", 22a''' are temporally regulated.

Temperature sensors T and pressure sensors P at the absorption units 22a, 22a', 22a", 22a''' are additionally applied for a temporal regulation of the process steps during absorption and regeneration phases.

Due to the plurality of absorption units 22a, 22a', 22a", 22a''' and to an interconnection of these with each other a quasi-continuous process is achievable, in which the absorption units 22a, 22a', 22a", 22a''' go through absorption and regeneration phases in a temporally offset manner (FIG. 5).

The absorption process 18a with the $CO_2$ absorber resin comprises an absorption phase AP as a precision-purification stage, in which the $CO_2$ is bonded to the absorption material, i.e. the solid amine, at a pressure between 1 $bar_{abs.}$ and 15 $bar_{abs.}$ and absorption heat 82a is obtained. The absorption heat 82a is conveyed out of the absorption units 22a, 22a', 22a", 22a''' by means of the heat carrier fluid 48a, as a result of which the absorption material is cooled by means of the heat carrier fluid 48a. The absorption heat 82a is fed to the biogas plant 98a, in particular to a fermenter. The bio-natural gas 52a can be obtained during this phase at the exit of the device and can be fed into the natural gas grid 64a.

Furthermore, the absorption process 18a comprises a regeneration phase RP, in which the $CO_2$ is expelled from the absorption material, i.e. the solid amine, the regeneration phase RP being split up in further phases I-V:

I. Pressure reduction/evacuation of the absorption material and methane recovery out of an empty space of the absorption unit 22a, 22a', 22a", 22a'''. Herein the evacuation preferably takes place isothermically.

II. Hydrogen feed-in from the power-to-gas plant 24a (however preferably optional)

III. Heating-up phase of the absorption material by means of the heat carrier fluid 48a, preferably up to a temperature of less than 120° C. Herein a waste heat 84a of a block heating and power station and/or of the membrane unit 26a and/or of the power-to-gas plant 24a and/or of one of the other absorption units 22a, 22a', 22a", 22a''' may be used. To this purpose a heating and cooling unit 30a is provided implemented as a heat exchanger (FIG. 6). Herein $CO_2$ is transported away either using the vacuum pump 68a (process without a power-to-gas plant 24a) and/or using $H_2$ as a purging gas (process with power-to-gas plant 24a and direct $H_2$ feed-in). The purging gas is herein fed in preferably at an increased pressure. In this case using the vacuum pump 68a can be dispensed with at least temporarily or even completely. Two pumps 92a, 94a are provided for a circulation of the heat carrier fluid 48a.

IV. Cooling-down phase of the absorption material by means of the heat carrier fluid 48a and heat integration respectively implementation of the TSA process by transfer of a waste heat 86a to another absorption unit 22a, 22a', 22a", 22a''' that is in a heating-up phase III. A residual waste heat 88a is fed to the biogas plant 98a, preferably to the fermenter.

V. Filling/pressurizing the absorption material with biogas 10a from the membrane unit 26a.

For the purpose of cooling, a cooling unit 28a implemented as an absorption chiller installation is provided, wherein a residual-heat coupling with the biogas plant 98a is effected (FIG. 6).

As has been explained above, a PSA process respectively a pressure exchange is realized between the absorption units 22a, 22a', 22a", 22a''' via the valves V1, V2, V9, V10, V11, V13. Herein pressure energy 90a is transferred from one absorption unit 22a, 22a', 22a", 22a''' to another absorption unit 22a, 22a', 22a", 22a''', in such a way that a pressure is increased at the beginning of the absorption phase AP and a pressure is reduced at the beginning of the regeneration phase RP. In the exemplary embodiment shown, the absorption unit 22a and the absorption unit 22a" are interconnected with each other and the absorption unit 22a' and the absorption unit 22a''' are interconnected with each other, to this purpose.

At the exit of the plant a flow sensor S2 and a $CH_4$ sensor S3 are arranged.

In FIGS. 7 and 8 further exemplary embodiments of the invention are shown. The following descriptions are substantially limited to the differences between the exemplary embodiments wherein regarding components, features and functions that remain consistent, the description of the first exemplary embodiment may be referred to. For distinguishing the exemplary embodiments the letters a, b and c have been added to the reference numerals. Regarding components with the same denomination, in particular regarding components with the same reference numerals, principally the drawings and/or the description of the first exemplary embodiment in FIGS. 1 to 6 may be referred to.

In FIGS. 7 and 8 two further simplified process presentations are shown, in which an absorption process 18b, 18c is used for gas processing in absorption units that are not shown in detail, in particular for precision cleaning of a generated methane 62b, 62c of a power-to-gas plant 24b, 24c, as a result of which previous to feed-in into a natural gas grid 64b, 64c, a high-grade purity of the methane 62b, 62c is achieved. The absorption units in FIGS. 7 and 8 are embodied corresponding to the absorption units 22a, 22a', 22a", 22a''' of the exemplary embodiment in FIGS. 1 to 6. Herein the process in FIG. 7 shows a process in which the gas processing is executed in a biogas plant 98b by means of a membrane process 14b, and the process in FIG. 8 shows a process in which the gas processing is executed in a biogas plant 98c without a membrane process.

In the process in FIG. 7, $CO_2$ respectively permeate 46b separated off by means of the membrane process 14b is conveyed to the power-to-gas plant 24b, and the permeate 46b is converted together with $H_2$ into methane and water in a methanization 60b in a method step 102b in a reactive process 104b. The product gas after the methanization 60b has purities greater than 90 volume percent of methane. In a downstream-connected method step 16b in an absorption process 18b a precision gas purification is then executed in the absorption units that are not shown in detail, as a result of which the $CO_2$ that has not been converted is separated off and the product gas is additionally dehydrated. The off-separated $CO_2$ is preferably re-fed to the methanization 60b as a pure $CO_2$ or as a $CO_2/H_2$ gas mixture. By means of the process according to FIG. 7, very high methane purities are achievable in the gas flow, which are preferably greater than 99.5 volume percent of methane 62b. Following this the obtained methane 62b is fed into the natural gas grid 64b. An ultrapure methane 100b resulting from the membrane process 14b, preferably with a purity greater than 99%, is directly fed into the natural gas grid 64b. As an alternative, the process gas of the membrane process 14b could also go through a subsequent purification in an adsorption process and/or absorption process.

In the process in FIG. 8, instead of an upstream $CO_2$ off-separation by means of a membrane process, the $CO_2$ contained in the biogas 10c is converted in a method step 102c in a reactive process 104c via a catalytic reaction with $H_2$ in a methanization unit 60c. Following this a precision gas purification of the product gas is executed in a downstream-connected method step 16c in an absorption process 18c in absorption units, in a manner analogous to the process in FIG. 7. Before the biogas 10c is conveyed to the power-to-gas plant 24c, the biogas 10c is dehydrated and pre-purified, in particular desulfurized.

REFERENCE NUMERALS 10 biogas
12 method step
14 membrane process
16 method step
18 absorption process
20 solid-matter absorber
22 absorption unit
24 power-to-gas plant
26 membrane unit
28 heating and/or cooling unit
30 heating and/or cooling unit
32 heating and/or cooling unit
34 tube
36 tube
38 wall
40 wall
42 power-to-gas plant
44 retentate
46 permeate
48 heat carrier fluid
50 housing
52 bio-natural gas
54 power
56 electrolysis
58 waste heat
60 methanization
62 methane
64 natural gas grid
66 compressor
68 vacuum pump
70 connection
72 connection
74 heat carrier fluid outlet
76 heat carrier fluid inlet
78 exit
80 water pump
82 absorption heat
84 waste heat
86 waste heat
88 residual waste heat
90 pressure energy
92 pump
94 pump
96 re-feed
98 biogas plant
100 methane
102 method step
104 reactive process
AP absorption phase
RP regeneration phase
I phase
II phase
III phase
IV phase
P pressure sensor
T temperature sensor
V valves
S sensor

The invention claimed is:

1. A method for processing biogas of a biogas plant, comprising:
performing in one method step a reactive process in which a methane-rich gas mixture is generated in a catalytically activated chemical process, and
performing in at least one further method step an adsorption and/or absorption process for a gas purification to achieve a methane purity greater than 99.5 volume percent, the adsorption and/or absorption process is executed as a precision purification in which a diminishing of a $CO_2$ concentration in the process gas is executed by utilizing a solid amine adsorber and/or absorber,
performing the reactive process as a pre-purification prior to the adsorption process and/or absorption process, and
performing the adsorption and/or absorption process as a subsequent purification.

2. The method according to claim 1, wherein at least one adsorption and/or absorption unit is cooled or heated in at least one method step.

3. The method according to claim 2, wherein heat energy is transferred from the at least one adsorption and/or absorption unit to at least one further adsorption and/or absorption unit.

4. The method according to claim 2, wherein pressure energy is transferred from the at least one adsorption and/or absorption unit to at least one further adsorption and/or absorption unit.

5. The method according to claim 2, wherein for a temperaturizing of the adsorption and/or absorption unit waste heat of a power-to-gas plant is utilized, wherein the waste heat is used for a regeneration of an adsorber and/or absorber material located in the at least one adsorption and/or absorption unit.

6. The method according to claim 2, wherein hydrogen is conveyed to the at least one adsorption and/or absorption unit.

7. The method according to claim 1, comprising a regeneration phase, in which $CO_2$ is expelled from the adsorption material and/or absorption material.

8. The method according to claim 1, wherein in the reactive process at least a methane-rich gas mixture is generated from a $CO_2$ source in a power-to-gas plant, and biogas is utilized as the $CO_2$ source.

9. The method according to claim 1, wherein the $CO_2$ contained in the biogas is converted in a method step in the reactive process via a catalytic reaction with $H_2$ in a methanization unit.

10. The method according to claim 1, carried out in a combination of a biogas plant with a power-to-gas-plant.

11. The method according to claim 1, wherein the solid amine adsorber and/or absorber selectively binds $CO_2$ in the further method step.

12. The method according to claim 2, wherein
the at least one adsorption and/or absorption unit is a plurality of adsorption and/or absorption units that each perform an absorption phase and a regeneration phase,
the regeneration phase includes
reducing or evacuating pressure from a solid amine of the amine adsorber and/or absorber as an absorption material and recovering methane out of an empty space of one of the plurality of adsorption and/or absorption units,
heating the solid amine of the amine adsorber and/or absorber as the adsorption material, via a heat carrier fluid, up to a predetermined temperature,
cooling the solid amine of the amine adsorber and/or absorber as the adsorption material, via the heat carrier fluid, by transferring waste heat to another one of plurality of adsorption and/or absorption units that is performing the heating of the solid amine of the amine adsorber and/or absorber as the adsorption material, and filling or pressurizing the solid amine of the amine adsorber and/or absorber as the adsorption material with the biogas.

13. The method according to claim 12, wherein thermally connected adsorption and/or absorption units of the plurality of adsorption and/or absorption units each perform a different phase of the regeneration phase and/or the absorption phase.

* * * * *